(12) United States Patent
Yoshioka et al.

(10) Patent No.: US 7,180,592 B2
(45) Date of Patent: Feb. 20, 2007

(54) PARTICLE SIZE DISTRIBUTION ANALYZER

(75) Inventors: Seiichiro Yoshioka, Kyoto (JP);
Yoshiyuki Okada, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 11/188,462

(22) Filed: Jul. 25, 2005

(65) Prior Publication Data

US 2006/0016968 A1   Jan. 26, 2006

(30) Foreign Application Priority Data

Jul. 26, 2004   (JP)   ............ P2004-217911

(51) Int. Cl.
*G01N 15/02* (2006.01)
(52) U.S. Cl. .................. 356/336
(58) Field of Classification Search ............. None
See application file for complete search history.

(56) References Cited

U.S. PATENT DOCUMENTS 6,249,344 B1 *   6/2001   Virag ................... 356/244

2002/0110487 A1   8/2002   Samsoondar
2003/0123057 A1   7/2003   Lemmo et al.

FOREIGN PATENT DOCUMENTS

| EP | 1 156 319 | 11/2001 |
|---|---|---|
| JP | 2002-243622 | 8/2002 |
| JP | 2005-017119 | 1/2005 |

* cited by examiner

Primary Examiner—Tu T. Nguyen

(57) ABSTRACT

A particle size distribution analyzer is equipped with cells, a light source, to irradiate particles in a cell and multiple photo-detectors that detect a light intensity of a diffraction light and/or a scattering light generated from the particles. An information processor calculates particle size distribution based upon light intensity signals transmitted from each of the photo-detectors. A movement retention unit moves the cells between a light irradiation position and withdrawal positions. A stop unit can stop one of the cells at the light irradiation position. A cell identification unit identifies a cell situated at the light irradiation position and transmits an identification signal of the cell to the information processor, which is equipped with a program switch unit that automatically switches to an appropriate program for controlling the operation of the analyzer corresponding to the cell identification signal.

22 Claims, 14 Drawing Sheets

PARTICLE SIZE DISTRIBUTION ANALYZER

BACKGROUND OF THE INVENTION

1. Field of the Invention

The present invention relates to a so-called diffraction/scattering particle size distribution analyzer where light is irradiated to particles dispersed within cells, and the particle size distribution of the above-mentioned particles is measured based upon the intensity distribution of diffraction and/or scattering lights (hereafter, as long as it is unnecessary to specifically distinguish the light, it is referred to as a scattering light), generated upon the light irradiation.

2. Description of Related Art

There are multiple types of cells per measuring method used for this type of particle size distribution analyzer, batch type cells, wet type flow cells and dry type cells are among those which are typically known. Conventionally, only one cell is exchangeably retained in a cell holder screwed to a body of the particle size distribution analyzer.

However, for the purpose of exchanging for a different type of cell, the entire cell holder has to be exchanged, so when performing the exchange, after screws of the pre-secured cell holder are loosened or removed and the cell holder is extracted from the analyzer body, or after withdrawing the cell holder to within a sample chamber where cells are contained so as not to be obstructive, it is necessary to re-secure, by screws, another cell holder to be used for measurement, so this operation is considerably time-consuming. In particular, a wet type flow cell holder is joined with a pre-processing mechanism, such as an ultrasonic probe for dispersion, a stirring wing, and a circulation pump, arranged in another section within the analyzer body, by pipes, and when extracting the cell holder to outside the analyzer body, it is necessary to detach the pipes; and to additionally remove the screws for securing the cell holder to the analyzer, complicating the operation.

Japanese Laid-Open Patent Application 2002-243622 discloses another type of analyzer designed by withdrawing a cell holder to a position within a sample chamber without being obstructive, wherein the pipes and cell holder are connected, constructing the pipe of a flexible material, such as silicon tube, or a foldable or elastic tube. However, since other types of cell holders (dry type or batch type cell holders) are extracted to outside the analyzer body when not in use, it is still necessary to remove the fixture screwed to the analyzer body when exchanging the cell holder. As described above, a lot of trouble is required when exchanging the cell, especially for different types of cells.

In addition, since software loaded in the conventional particle size distribution analyzer only supports only one measuring method for either cell, if a cell is exchanged for a different type, software that supports the exchanged cell type must be loaded, with the problem of operability. In addition, an error may occur due to negligence relating to the software exchange. Although problems of relationship become remarkable especially when a cell is exchanged for one of a different type, these problems will occur to no small extent when making an exchange for the same type of cell (but one having different content).

SUMMARY OF THE INVENTION

It is an objective of the present invention to resolve the above-mentioned problems in a single stroke, to save labor required for the cell exchange in this type of particle size distribution analyzer, and to automatically switch to another program for controlling the operation of the analyzer according to the cell or the cell type associated with the cell exchange.

In other words, the particle size distribution analyzer relating to the present invention is a particle size distribution analyzer provided with cells; a light source that irradiates a light to particles contained in the cells; multiple photo-detectors that detect the light intensity of diffraction light and/or a scattering light generated from the particles irradiated by the light; and an information processor that calculates the particle size distribution of the above-mentioned particles based upon light intensity signals transmitted from each of the above-mentioned photo-detectors.

It is further provided with a movement retention means that retains multiple cells to be movable between a light irradiation position irradiated by the above-mentioned light and withdrawal positions established at different positions from the light irradiation position; a stop means that stops either cell at the above-mentioned light irradiation position; and a cell identification means that identifies the cell situated at the light irradiation position and transmits an identification signal of the cell, wherein the information processor is equipped with operation control program storage where an operation control program comprising a program for controlling the operation of the above-mentioned particle size distribution analyzer with respect to each of the above-mentioned cells, is stored; and a program switch means that receives the cell identification signal transmitted from the above-mentioned identification means, and that automatically switches to another operation control program corresponding to the cell indicated by the cell identification signal.

With this analyzer, while multiple cells are retained in the movement retention means, any of the cells are selectively moved to the light irradiation position, enabling the irradiation of light onto the cell, enabling automatic switching to another program for controlling the operation of the particle size distribution analyzer corresponding to the cell. Therefore, the time required for exchanging the cell can be shortened, reducing the operator burden and errors.

Needless to say, cell exchange includes exchanges for different types of cells, and exchanges for the same type of cell, but of different content.

For cell identification, a mechanism to identify a shape of a cell itself or to read a bar code attached to a cell can be used. However, in order to identify a cell more easily without affecting measurements, it is desirable that the cell identification means identifies a cell holder that retains a cell in the light irradiation position, and transmits the identification signal of the cell.

If the cell situated at the light irradiation position is withdrawn, another cell automatically moves to the light irradiation position, and to facilitate greater simplification of the cell exchange, it is desirable that the particle size distribution analyzer be additionally equipped with a cell support member for integrally supporting multiple cells, with the movement retention means moving the above-mentioned cell support member along a predetermined track.

In order for different types of cells, such as batch type cells, wet type flow cells and dry type cells, to be exchangeable, it is desirable that the movement retention means be constructed to be capable of retaining multiple different types of cells.

As a specific embodiment of the above-mentioned movement retention means, a movement retention means equipped with a rail arranged along a track, where the cells are movably mounted along the rail can be provided.

Further, if the stop means utilizes a latch mechanism, cell positioning can be accurately and easily performed.

As described above, the present invention relates to a particle size distribution analyzer where a simple movement operation along the movement retention means can substitute for complicated attachment/detachment operations to/from the particle size distribution analyzer when accomplishing cell exchange, and where a program for controlling the operation of the analyzer can be automatically switched to another according to the cell type associated with the cell exchange can be provided, enabling the time required for switching measurements to be shortened. In addition, the burden on an operator can be reduced, and errors prevented.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

An embodiment of the present invention is described hereafter, with reference to the drawings.

Figure 1:
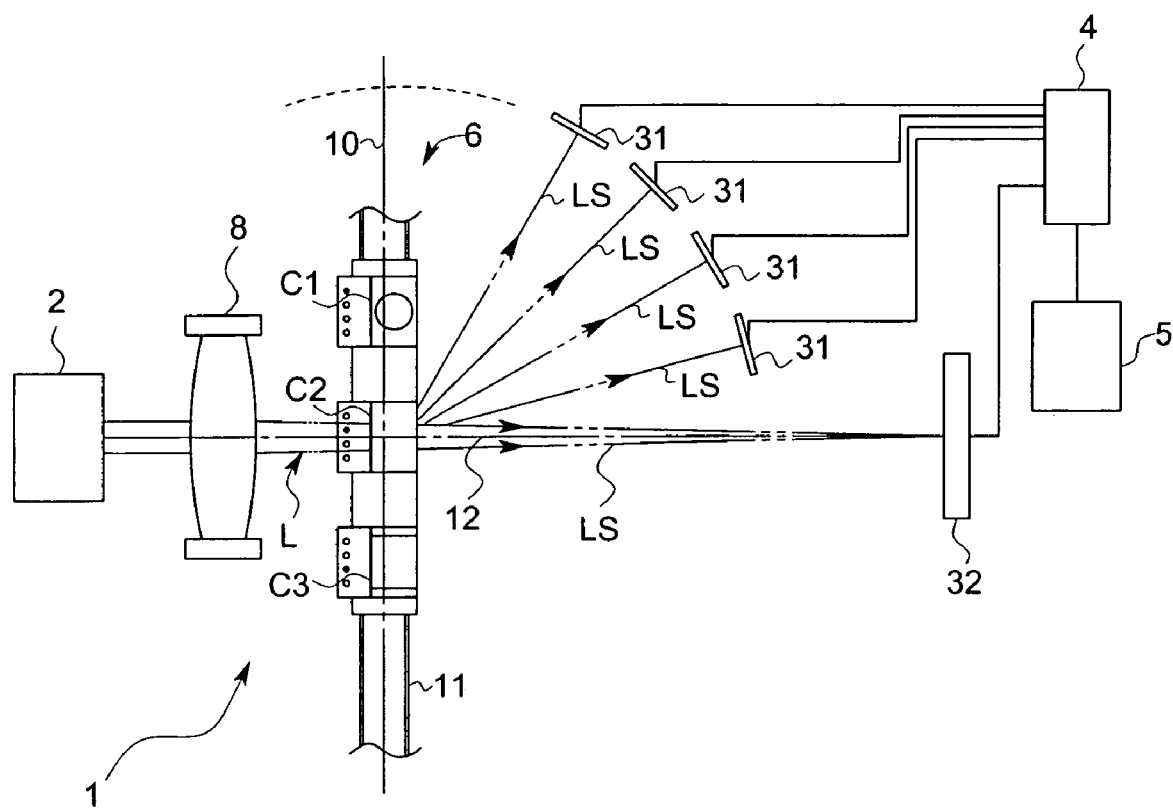
FIG. 1 is a pattern overall view that shows the construction of the particle size distribution analyzer in an embodiment of the present invention.
Figure 2:
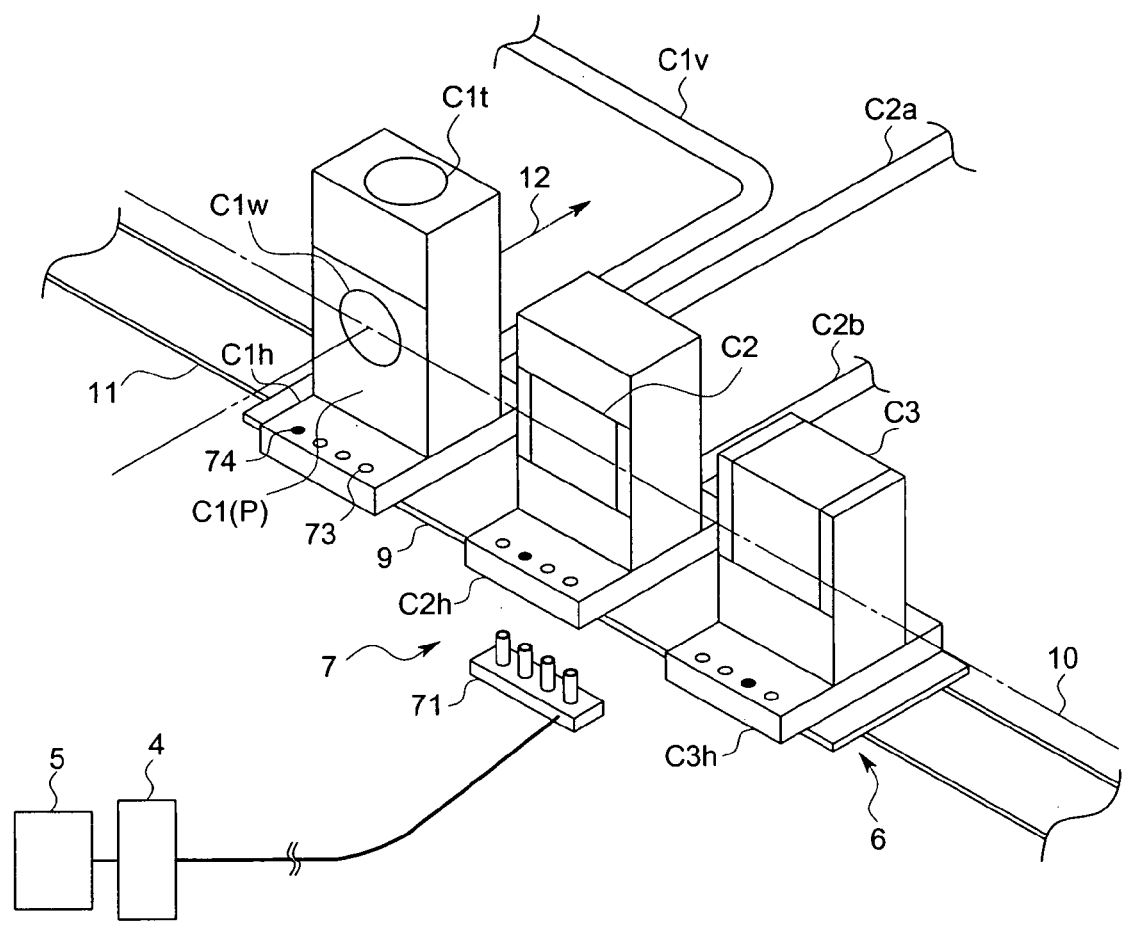
FIG. 2 is a perspective view that shows the vicinity of the movement retention means in the embodiment.

A particle size distribution analyzer 1 relating to the present embodiment is designed such that a theory is used where a scattering pattern (an angle distribution of scattering light intensity) of a scattering light LS generated on the occasion of irradiating an irradiation light L to particles is determined according to a particle size, and the detection of the above-mentioned scattering pattern results in the measurement of the particle size distribution based upon an MIE scattering theory. The pattern schematic diagram of the particle size distribution analyzer 1 is shown in FIG. 1 and FIG. 2. In the figures, the symbols C1, C2 and C3 indicate cells, where samples where particles comprising the subject of measurement, are dispersed in a dispersion medium, are contained. For the above-mentioned dispersion medium, water and air are used in the case the wet type cell and in the case of the dry type cell, respectively. The symbol 2 indicates a light source that irradiates the irradiation light L on the above-mentioned cells C1, C2 or C3. In the present embodiment, as this light source, for example, use is made of a semiconductor laser that irradiates a coherent laser beam. The symbols 31 and 32 indicate photo-detectors arranged around the periphery of the above-mentioned cells C1, C2 and C3, and these photo-detectors detect the light intensity of the scattering lights LS generated from the particles irradiated by the light L. The symbol 4 indicates a signal processor composed of a buffer, an amplifier, and the like, where each of the scattering light intensity signals transmitted from the above-mentioned photo-detectors 31 and 32 is received and converted. The symbol 5 indicates an information processor that calculates the particle size distribution of the above-mentioned particles based upon the values of each scattering light intensity signal processed by the signal processor 4. The symbol 8 indicates a convex lens established so as to converge the transmitted light L at the center of the reception surface of the photo-detector 32.

In the present embodiment, a cell support member 9 that integrally supports multiple cells C1, C2 and C3, which differ from each other, within an unshown cell compartment is established. A movement retention means 6 is additionally established.

The cell support member 9, for example, is in a long plate-state, and the above-mentioned cells C1, C2 and C3 are linearly retained along its long side. Specifically, the above-mentioned cells C1, C2 and C3 are detachably retained by cell holders C1h, C2h and C3h, respectively. Furthermore, in FIG. 2, although the cell support member 9 retains the above-mentioned three types of cells C1, C2 and C3, which are different from each other, it can also retain multiple cells, which are of the same type.

Here, cell holders C1h, C2h and C3h are provided for retaining the cells C1, C2 and C3 in the cell support member 9, respectively, and have, for example, a rectangular shape. Their long sides have a wider width along the optical axis compared to that of the cell support member 9 attached to the lower surfaces of the cell holders C1*h*, C2*h* and C3*h*, and the above-mentioned cells C1, C2 and C3 are detachably mounted onto their upper surfaces, respectively.

The cell C1 is a dry type, and is integrated with the cell holder C1*h*. As shown in FIG. 2, a sample inlet C1*t* for putting particles in is established on the upper side; a vacuum pipe C1*v* for sucking the particles is mounted to the lower side; and a round-shaped window C1*w*, or the like, for irradiating the irradiation light L to the put particles is established.

The cell C2 is a wet flow type, designed so that both the upside and the downside are retained on the cell support member 9 by the wet type cell holder C2*h*. For the purpose of dispersing particles in a liquid solvent, such as water, in the cell C2, an unshown circulation pump and particle stirrer, such as an ultrasonic probe, are established on a liquid circulation passage. In the diagram, the symbols C2*a* and C2*b* represent pipes that form the liquid circulation passage, and are connected with lead-in/out ports of the cell C2, respectively.

The cell C3 is a so-called batch type suitably used when measuring a very small quantity of samples, and is designed so that the lower side is retained in the cell support member 9 by the batch type cell holder C3*h*.

The movement retention means 6 retains the above-mentioned cell support member 9 to be movable on a rail 11 arranged on the floor surface of the above-mentioned cell compartment along a track 10, comprising a straight line perpendicular to an optical axis 12. With this construction, the above-mentioned cells C1, C2 and C3 become movable between a light irradiation position P, which is the crossing point of the optical axis 12 and the above-mentioned track 10, and withdrawal positions other than the light irradiation position P.

On this occasion, in order that the above-mentioned cells C1, C2 and C3 situated at the withdrawal positions not block the scattering light LS that enters into the photo-detectors 31 and 32, the positions of the photo-detectors 31 and 32 are established, for example, within a plane vertical to the track 10.

Further, a stop unit 18 where a latch mechanism using a spring 181, etc. is utilized as a mechanism to stop the cells C1, C2 or C3 moving toward the light irradiation position P, is established at the position P.

In addition, a cell identification means 7 that identifies whether the cell situated at the above-mentioned light irradiation position P is C1, C2 or C3, and that transmits an identification signal of the cell is established in the particle size distribution measuring analyzer 1 relating to the present embodiment. Then, the above-mentioned information processor 5 receives the cell identification signal, and switches to another program so as to correspond to the operation of the above-mentioned particle size distribution analyzer 1 according to the cell type.

Figure 3:
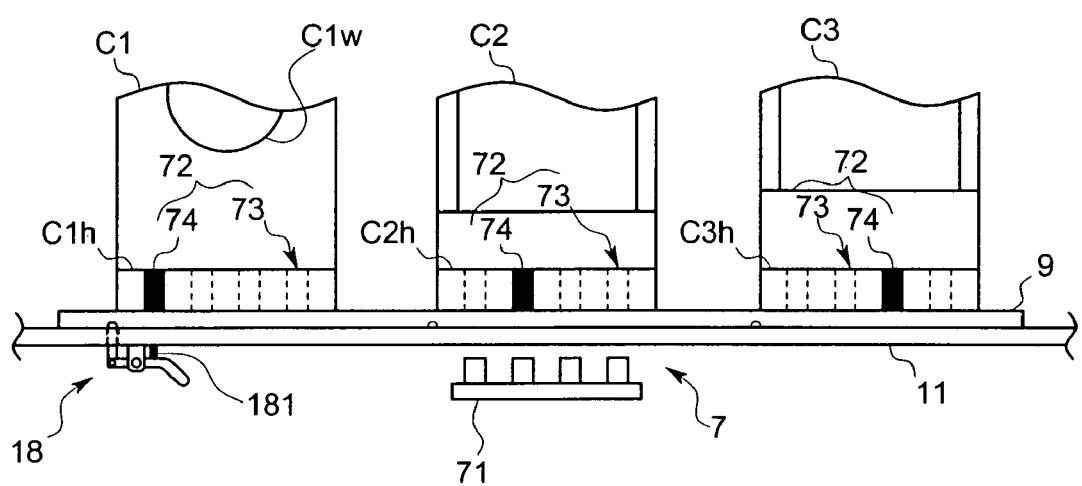
FIG. 3 is a pattern diagram that shows the construction of the cell identification means in the embodiment.

As shown in FIG. 3, the cell identification means 7 is provided with a hole sensor 71, and identifies a section to be identified 72 in the cell holder C1*h*, C2*h* or C3*h*. Here, the sections to be identified 72 are constructed such that multiple holes 73 are linearly established with a constant interval at the end of cell holders C1*h*, C2*h* and C3*h*, respectively, and in the portions where the cells C1, C2 and C3 are not mounted, and a magnet 74 is arranged at one of the holes 73, which is positioned differently per cell type. Further, the hole sensor 71 is established under the cell holders C1*h*, C2*h* or C3*h* so as to correspond to each set of holes 73 established in the cell holders C1*h*, C2*h* and C3*h* when the either the above-mentioned cell C1, C2 or C3 is arranged at the light irradiation position P. Then, the detection of the section to be identified 72 in the cell holder situated at the light irradiation position P results in the identification of the cell C1, C2 or C3, and an identification signal of the cell is transmitted.

Figure 4:
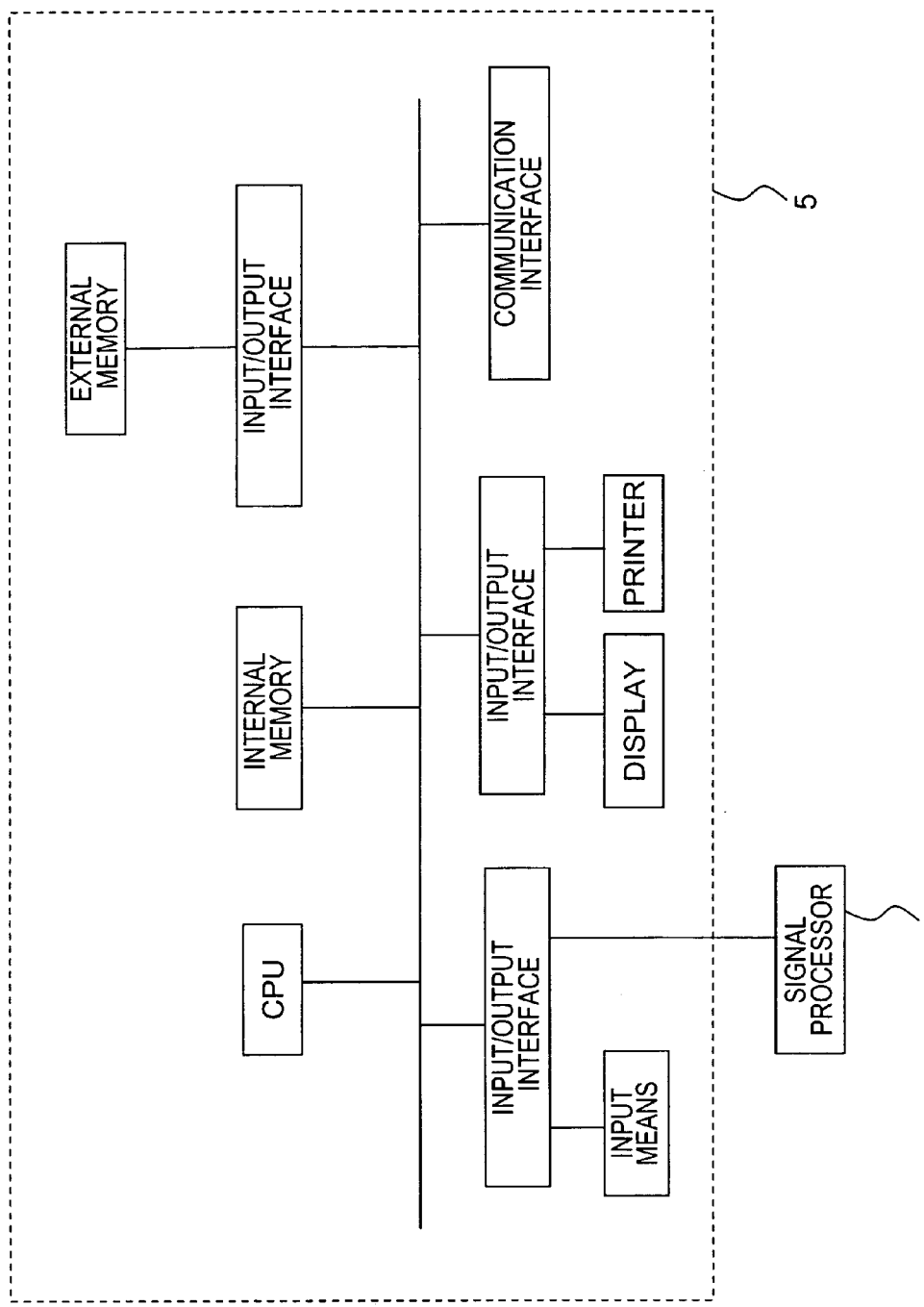
FIG. 4 is a configuration diagram that shows the configuration of the information processor in the embodiment.
Figure 5:
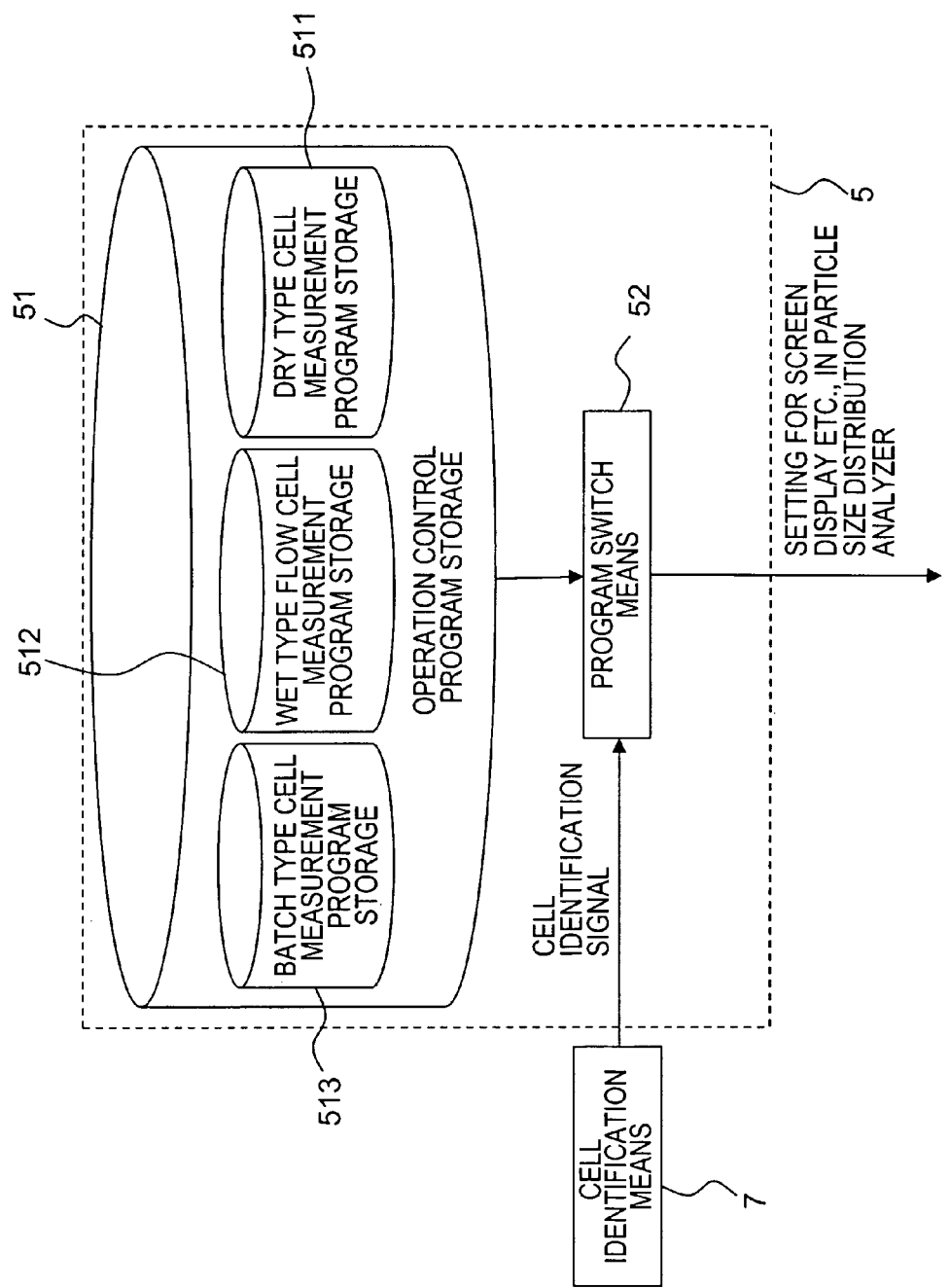
FIG. 5 is a function block diagram that shows the function configuration of the information processor in the embodiment.

The above-mentioned information processor 5, is shown in FIG. 4 and 5 An operation control program comprising a program for controlling the operation of the particle size distribution analyzer 1 corresponding to the cell type, is stored in the operation control program storage 51. In the present embodiment, the operation control program storage 51 contains a dry type cell measurement program storage 511 where a measurement program corresponding to the dry type cell C1 is stored, a wet type flow cell measurement program storage 512 where a measurement program corresponding to the wet type flow cell C2 is stored, and a batch measurement program storage 513 where a measurement program corresponding to the batch type cell C3 is stored 4, is a general purpose or customized computer equipped with a CPU, memories and input/output interfaces, and the cooperation of the CPU and the peripheral equipment by complying with a predetermined program stored in a predetermined region in the above-mentioned memories also enables the demonstration of functions as an operation control program storage 51, a program switch means 52, and the like.

Figure 6:
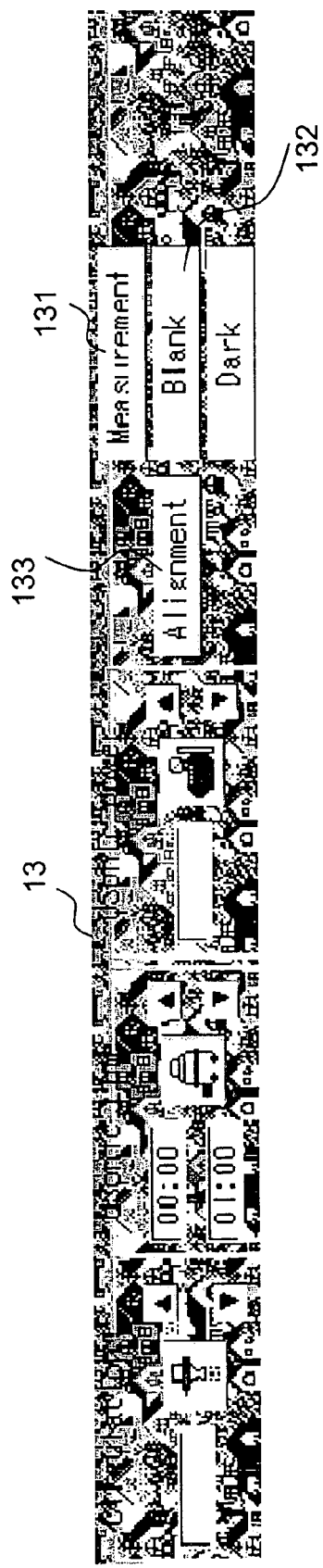
FIG. 6 is a view that shows a measurement screen corresponding to a dry type cell in the embodiment.
Figure 7:
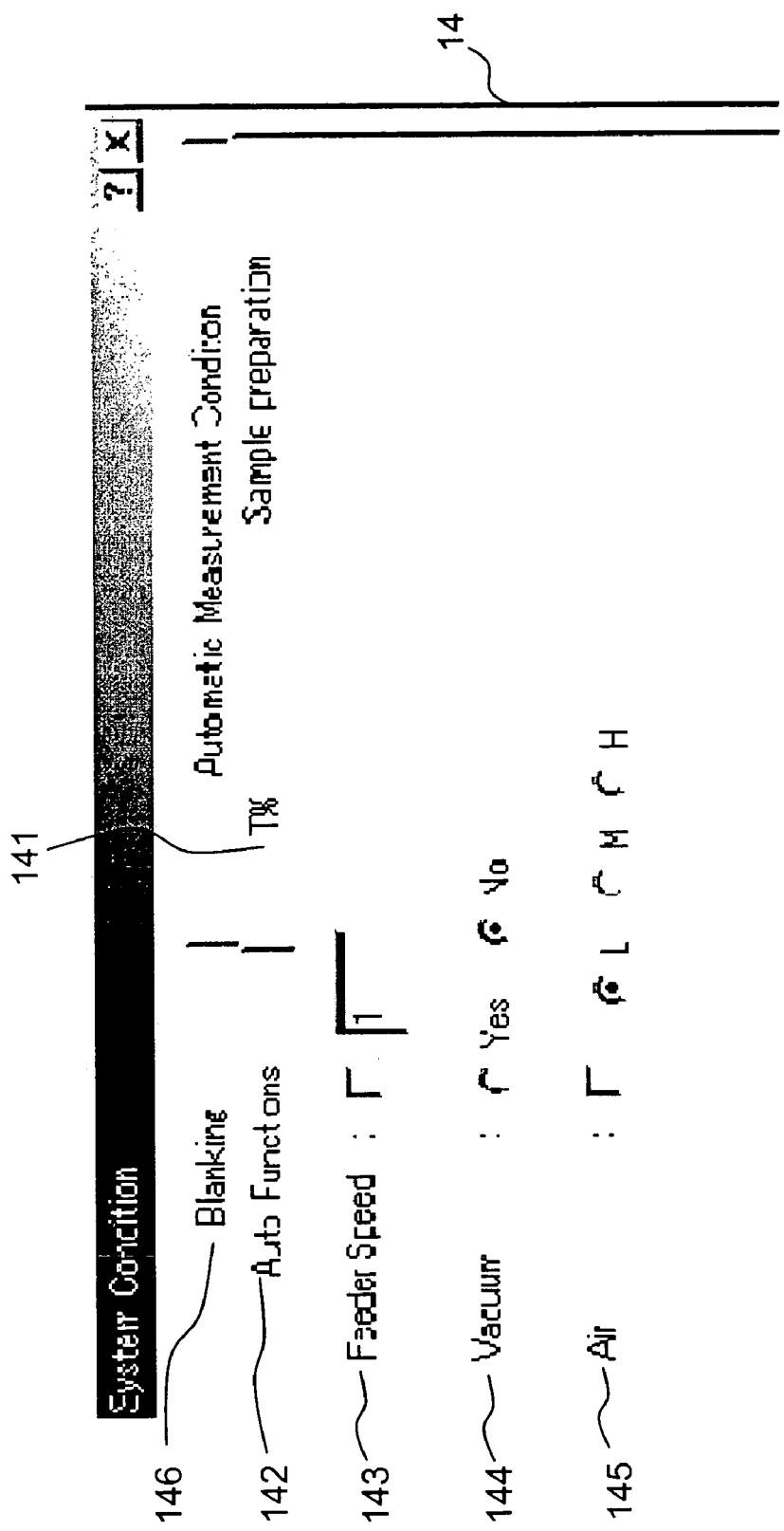
FIG. 7 is a view that shows a condition setting dialog corresponding to a dry type cell in the embodiment.

With the dry type cell measurement program, a measurement screen 13 shown in FIG. 6 and a condition setting dialog 14 shown in FIG. 7 are displayed on the screen of the particle size distribution analyzer 1, respectively. In addition, setting for a dry type operational processing, an initialization processing and a dry type measuring sequence is performed. The measurement screen 13 is a screen for a dry type measurement 131, a blank measurement 132 and an optical axis alignment 133, and the like. The condition setting dialog 14 is for the detailed setting on the occasion of the dry type measurement. For specific condition setting, there are a temperature setting 141, a setting for printing or automatic saving 142, a sample adjustment (a feeder speed setting 143, a vacuum setting 144 and a compressed air-pressure setting 145), a time setting for blank measurement 146, and the like.

Figure 8:
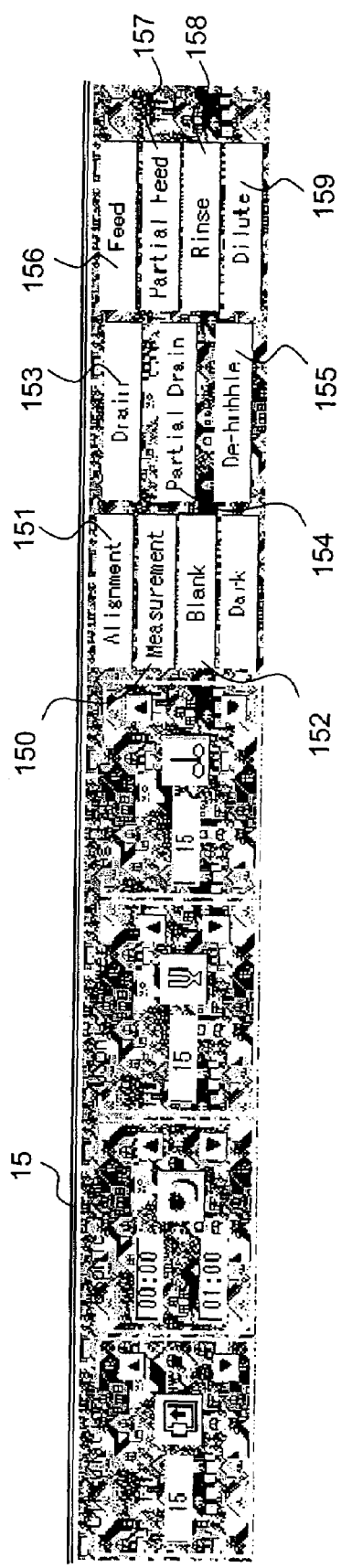
FIG. 8 is a view that shows a measurement screen corresponding to a wet type flow cell in the embodiment.
Figure 9:
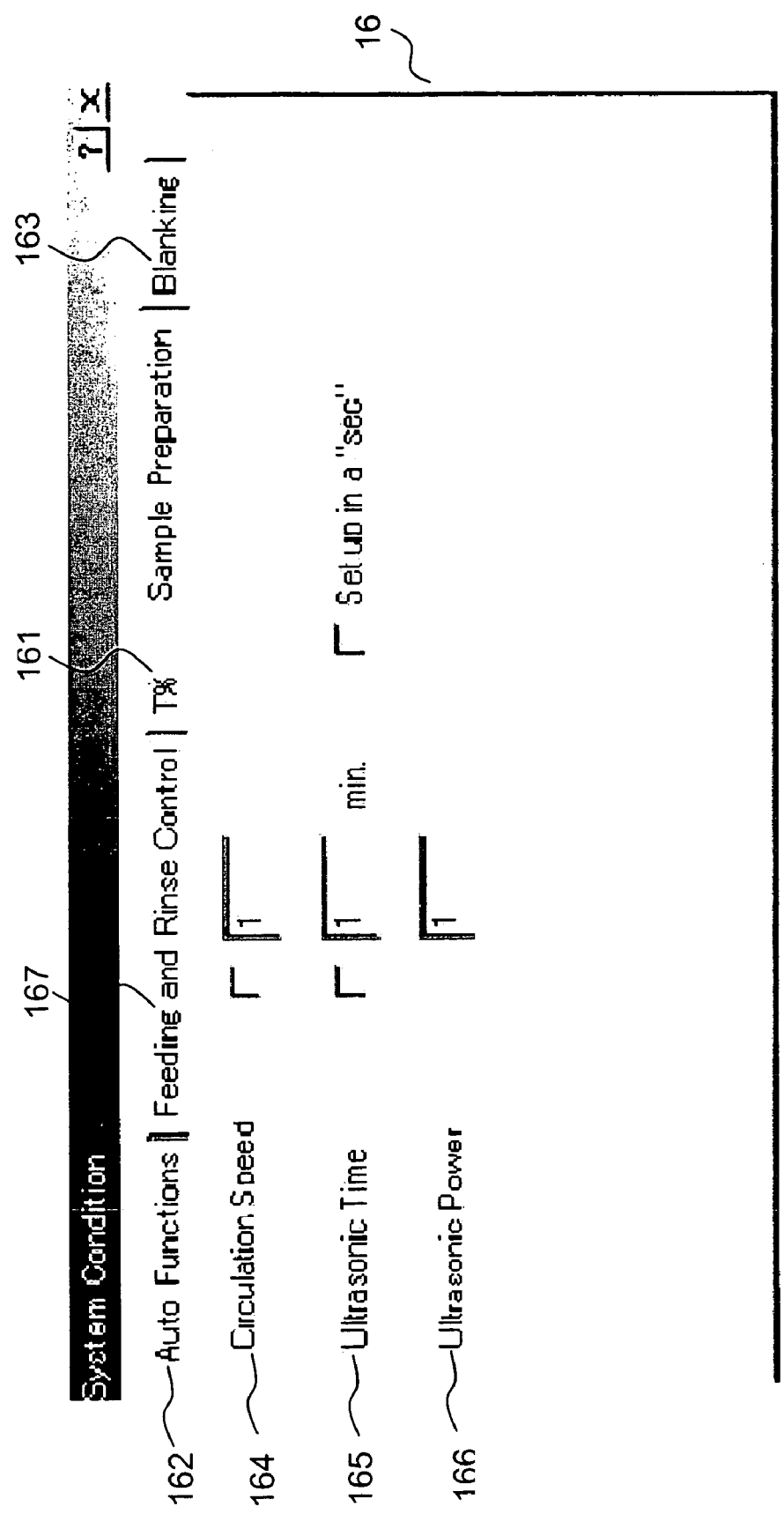
FIG. 9 is a view that shows a condition setting dialog corresponding to a wet type flow cell in the embodiment.

With the wet type flow cell measurement program, a measurement screen 15 shown in FIG. 8 and a condition setting dialog 16 shown in FIG. 9 are displayed on the screen of the particle size distribution analyzer 1, respectively. In addition, setting for a wet type operational processing, an initialization processing and a wet type measurement sequence is performed. The measurement screen 15 is a screen for a wet type measurement 150, an optical axis alignment 151 and a blank measurement 152 in addition to for draining water 153, partially draining water 154, de-bubbling 155, automatic feeding of a dispersion medium 156, automatic partial feeding of a dispersion medium 157, rinsing 158, and automatic sample dilution 159, and the like. The condition setting dialog 16 is for the detailed setting on the occasion of the wet type measurement. For the specific condition setting, there are a temperature setting 161, a setting for automatic printing or automatic saving 162, a time setting for blank measurement 163, sample adjustment (a setting for circulation speed 164, a setting for ultrasonic time 165 and a setting for ultrasonic power 166), and a setting for the number of rinsing processes 167, and the like.

Figure 10:
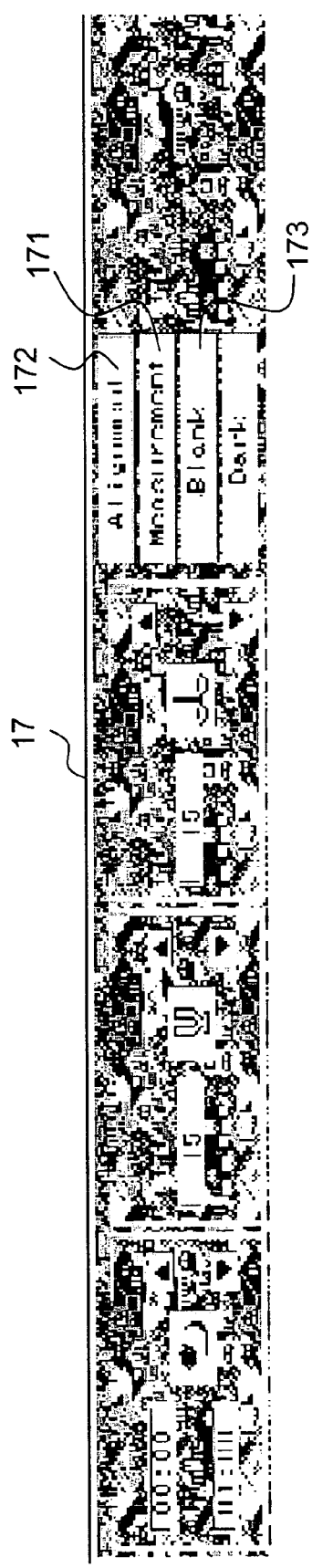
FIG. 10 is a view that shows a measurement screen corresponding to a batch type cell in the embodiment.

With the batch measurement program, a measurement screen 17 shown in FIG. 10 is displayed on the screen, and the setting for an operation processing, an initialization processing or a measurement sequence is performed. The measurement screen 17 is for batch type measurement 171, an optical axis alignment 172 and a blank measurement 173.

The program switch means 52 receives a cell identification signal transmitted from the above-mentioned cell identification means 7, and specifies the cell type according to the cell identification signal. Then, the program switch means 52 switches to another program in order to correspond to the operational specifications of the particle size distribution analyzer 1 corresponding to the cell type, enabling automatic switching of the screen display or processing conditions.

Next, an example of the procedure for the particle size distribution measurement using the present analyzer 1 is described hereafter.

Figure 11:
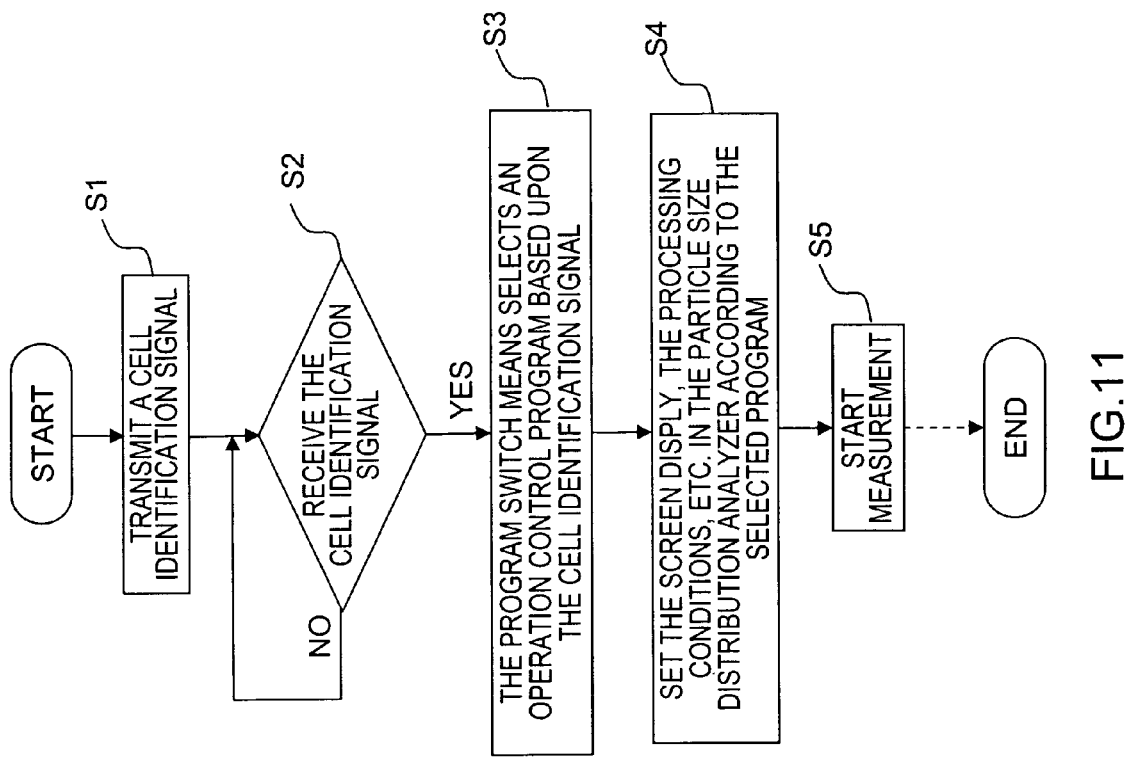
FIG. 11 is a flow chart that shows the operation of switching the particle size distribution analyzer in the embodiment.
Figure 12:
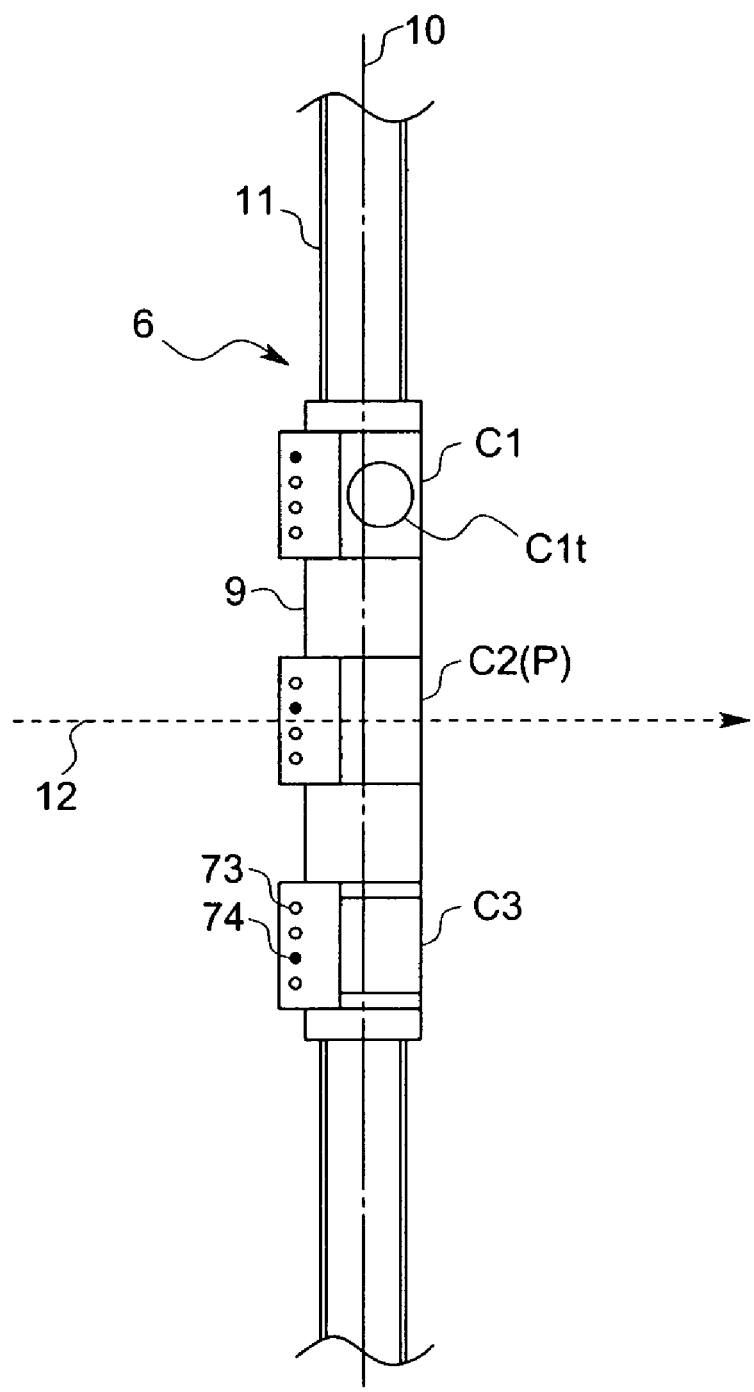
FIG. 12 is a plane view that shows a case when a wet type flow cell is selected in the embodiment.

First, an operator slides the cell support member 9 on the rail 11, and moves a desired cell (for example, C2) to the light irradiation position P, as shown in FIG. 12. Whether the cell C2 is situated on the light irradiation position P can be determined by a click-stop touch with the latch mechanism. Then, as shown in FIG. 11, the cell identification means 7 identifies the cell, and transmits the identification signal of the cell (Step S1). The program switch means 52 receives this transmitted cell identification signal (Step S2), and selects a program corresponding to the cell C2 and starts the program (Step S3). Then, the screens shown in FIG. 8 and FIG. 9 are displayed on the screen of the particle size distribution analyzer 1 based upon the selected program, and the processing conditions are set (changed) (Step S4). Subsequently, if the measurement starts as with a conventional method (Step S5), the particle size distribution of the particles contained in the cell C2 can be obtained.

In the case of measuring the particles in another cell C1 or C3, similar to the above-mentioned case of the cell C2, the cell support member 9 may simply be slid.

Furthermore, the pipes C1v and C2a & C2b are connected to the cells C1 and C2, respectively. As described above, the pipes C1v, C2a and C2b are partially or entirely flexible. Since the pipes can change their shape due to the movement of the cells C1 and C2, attachment/detachment operations are easy, and will never obstruct the movement of the cells C1 and C2, respectively.

Figure 13:
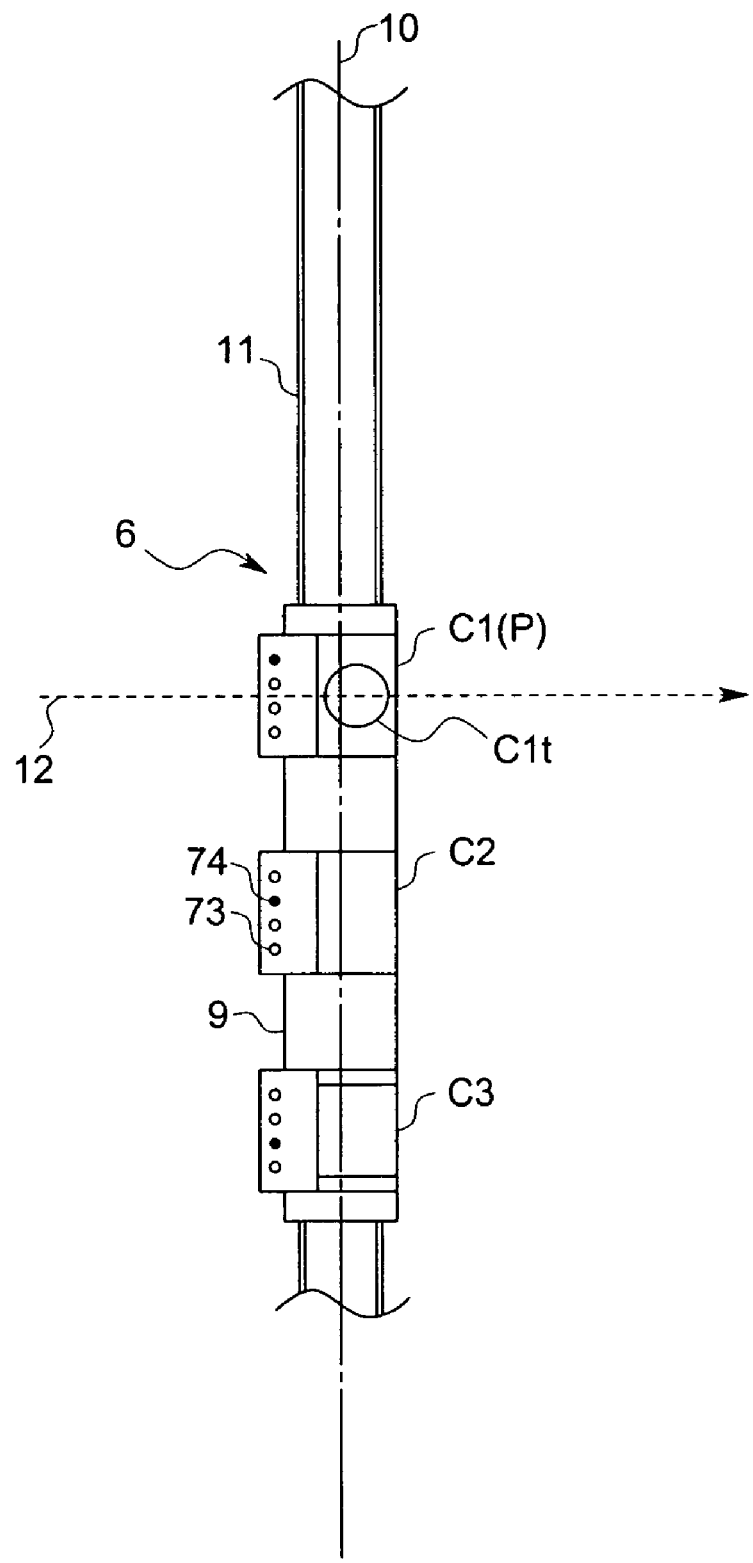
FIG. 13 is a plane view that shows a case when a dry type cell is selected in the embodiment; and, FIG. 14 is a plane view that shows a case when a batch type cell is selected in the embodiment.
Figure 14:
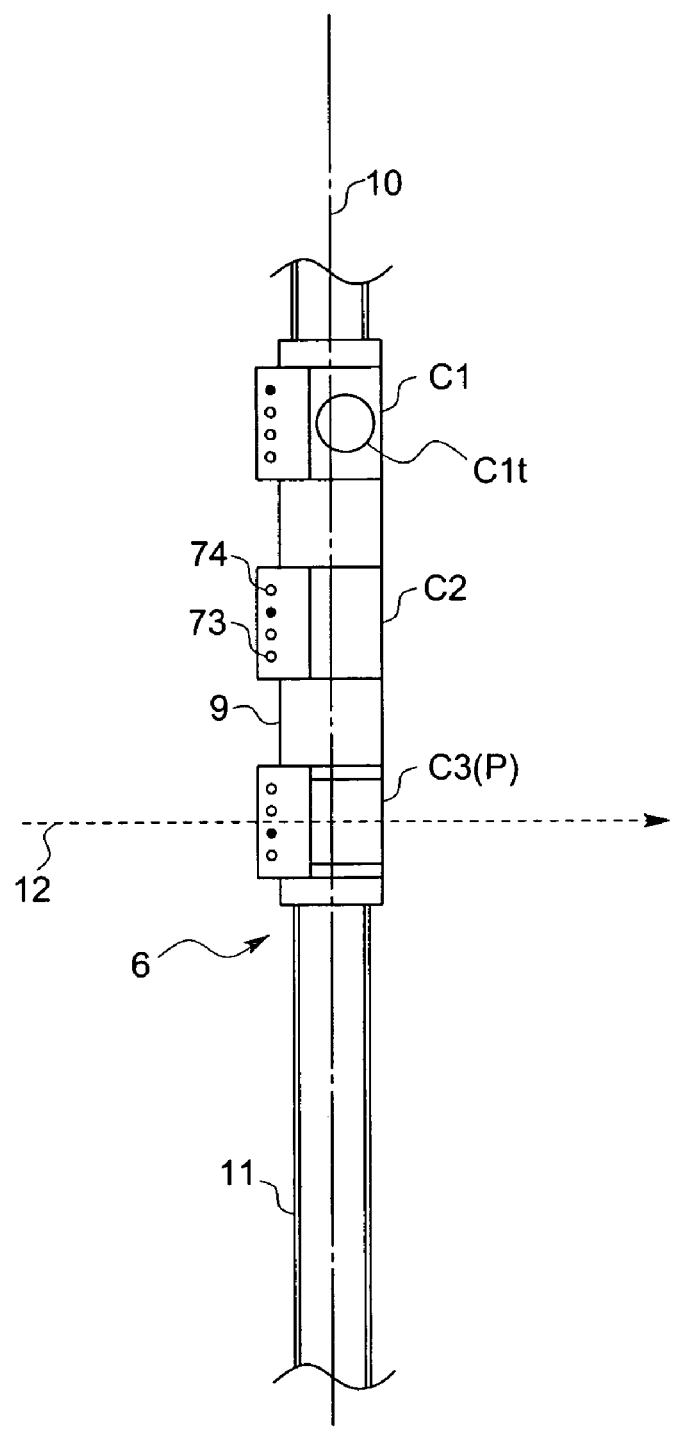

FIG. 13 and FIG. 14 show a state in which the dry type cell C1 and the batch type cell C3 are finished, moving to the light irradiation position P from the withdrawal positions, respectively As described above, according to the present embodiment, when accomplishing cell exchange, each of the cell C1, C2 and C3 can be merely slid by utilizing the movement retention means 6. Since it is unnecessary to attach or detach the cells, the workability will never be delayed. Associated with the exchange, a program for controlling the operation of the analyzer can be automatically switched according to the cell type, and the time required for switching the measurement can be shortened. In addition, the burden on an operator can be reduced, and, whether or not the desired cell C1, C2 or C3 is set on the light irradiation position P can be confirmed merely on the screen, preventing operating errors.

Since the latch mechanism is included, each of the cells C1, C2 and C3 can be accurately and easily positioned to the light irradiation position P.

In addition, the multiple cells C1, C2 and C3 are retained on the one cell support member 9, and the withdrawal of the cell C1, C2 or C3 from the light irradiation position P and the movement of the cell C1, C2 or C3 to the light irradiation position P can be simultaneously performed.

In addition to the above-mentioned construction, in the present embodiment, since having a straight rail 11 in the movement retention means 6 results in the linear alignment of the moved cells C1, C2 and C3 in the withdrawal positions, areas of the cells C1, C2 and C3 that may block the scattering light LS can be reduced, and areas where the optical detectors 31 and 32 are arrangeable can become greater.

Furthermore, the present invention is not limited to the above-mentioned embodiment.

For example, even though the cells are the same type with each other, if subjects for measurement contained in the cells are different from each other, the settings may be different (for example, the setting for the refractive index), so even if the cell is exchanged for the same type, it can be designed to automatically switch from to another program corresponding to the cell.

In the above-mentioned embodiment, the particle size distribution analyzer using a dry type cell, a wet type flow cell and a batch type cell has been described. However, the cells are not limited to this combination, but two types, for example, a dry type cell and a wet type flow cell, can be used. Alternatively, another combination of two types, the wet type flow cell and the batch type cell, can also be used.

The sections to be identified used for identification by the cell identification means is not limited to one where a magnet is arranged in a hole, but it can be a bar code, or the sections to be identified can be established on the side of the cell holder along a light incident direction, respectively.

In addition, although there are four holes in the above-mentioned embodiment, for example, the holes can be established with the number of the cell types, and the number of the holes where the magnet is arranged can also be changed.

Further, the track shall not be limited to a straight line, and for example, it can be curved.

Further, for the movement retention means, not only one using a rail but another using a robot arm or belt conveyor can be used.

In addition, if the movement retention means is equipped with an actuator for moving the cells, it becomes unnecessary for an operator to move the cells, so the labor for the exchange of the cells or the cell holders can be additionally saved.

Further, if the cell support member is detachable to the measuring analyzer body and a plural number can be attached, and in addition, if multiple cell support members are connectable to each other, they can retain the number of the cells the occasion demands, so movement between the light irradiation position and the withdrawal positions and securing at each position can be simultaneously performed.

In addition, if an exchangeable adaptor where the cell support member and various cells are secured at an appropriate distance, respectively, is detachable so as to irradiate the irradiation light to samples, it becomes possible to retain various types of cells or cell holders for any purpose, so this analyzer can also support the utilization of any existing cells or unknown cells, which will be introduced in the future.

Needless to say, the particle size distribution analyzer does not have to have construction where the information processor, the signal processor, the controller of the particle size distribution analyzer and the analyzer body are integrated, but, for example, the signal processor and the information processor can be established outside the particle size distribution analyzer. Alternatively, the information processor, the signal processor and the controller of the particle size distribution analyzer can be established outside of the analyzer body, as well. Otherwise, the present invention can be variously modified within the scope of its concept.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A particle size distribution analyzer comprising;
multiple cells;
a light source that irradiates light to particles contained in the cells;
multiple photo-detectors that detect the light intensity of a diffraction light or a scattering light generated from the particles irradiated by the light; and
an information processor that calculates a particle size distribution of the particles based upon light intensity signals transmitted from each of the photo-detectors, wherein,
the particle size distribution analyzer further comprises a movement retention unit that retains the multiple cells to be movable between a light irradiation position irradiated by the light from the light source and withdrawal positions established at different positions from the light irradiation position;
a stop unit that selectively stops one of the multiple cells at the light irradiation position; and
a cell identification means that identifies the cell situated at the light irradiation position, and transmits an identification signal for that cell; and,
the information processor is equipped with an operation control program storage unit for storing a plurality of operation control programs, each comprising a program for controlling the operation of the particle size distribution analyzer with respect to one of the multiple cells, and a program switch means that receives the cell identification signal transmitted from the cell identification means, and automatically switches to another of the stored operation control programs corresponding to the cell indicated by the cell identification signal.

2. A particle size distribution analyzer according to claim 1, wherein, the cell identification unit identifies a cell holder where the cell situated at the light irradiation position is retained, and transmits the identification signal of the cell.

3. The particle size distribution analyzer according to claim 2, wherein, the particle size distribution analyzer further comprises a cell support member that integrally supports the multiple cells, and the movement retention means moves the cell support member along a predetermined track.

4. The particle size distribution analyzer according to claim 2, where the movement retention means can retain multiple different types of cells.

5. The particle size distribution analyzer according to claim 2, wherein, the movement retention means comprises a rail arranged along the track, and moves the cells along the rail.

6. The particle size distribution analyzer according to claim 2, wherein, a latch mechanism is utilized for the stop unit.

7. The particle size distribution analyzer according to claim 1, wherein, the particle size distribution analyzer further comprises cell support member that integrally supports the multiple cells, and the movement retention means moves the cell support member along a predetermined track.

8. The particle size distribution analyzer according to claim 7, where the movement retention means can retain multiple different types of cells.

9. The particle size distribution analyzer according to claim 7, wherein, the movement retention means comprises a rail arranged along the track, and moves the cells along the rail.

10. The particle size distribution analyzer according to claim 7, wherein, a latch mechanism is utilized for the stop unit.

11. The particle size distribution analyzer according to claim 1, where the movement retention means can retain multiple different types of cells.

12. The particle size distribution analyzer according to claim 11, wherein, the movement retention means comprises a rail arranged along the track, and moves the cells along the rail.

13. The particle size distribution analyzer according to claim 11, wherein, a latch mechanism is utilized for the stop unit.

14. The particle size distribution analyzer according to claim 1, wherein, the movement retention means comprises a rail arranged along the track, and moves the cells along the rail.

15. The particle size distribution analyzer according to claim 14, wherein, a latch mechanism is utilized for the stop unit.

16. The particle size distribution analyzer according to claim 1, wherein, a latch mechanism is utilized for the stop unit.

17. The particle size distribution analyzer of claim 1 further including a display unit and the information processor displays on the display unit a measurement screen for a measurement and a condition setting dialog for a detailed condition setting on the occasion of a measurement.

18. A particle size distribution analyzer comprising:
multiple cells;
a light source that irradiates light to particles contained in the cells;
multiple photo-detectors that detect the light intensity of a diffraction light or a scattering light generated from the particles irradiated by the light; and
an information processor that calculates a particle size distribution of the particles based upon light intensity signals transmitted from each of the photo-detectors, wherein,
the particle size distribution analyzer further comprises a movement retention unit that retains the multiple cells to be movable between a light irradiation position irradiated by the light from the light source and withdrawal positions established at different positions from the light irradiation position;
a stop unit that selectively stops one of the multiple cells at the light irradiation position;
a cell identification means that identifies the cell situated at the light irradiation position, and transmits an identification signal for that cell; and
a cell support member that integrally supports the multiple cells;
the information processor is equipped with an operation control program storage unit for storing a plurality of operation control programs, each operation control program controls the operation of the particle size distribution analyzer with respect to one of the above-mentioned cells, and a program switch means that receives the cell identification signal transmitted from the cell identification means, and automatically switches to another operation control program corresponding to the cell indicated by the cell identification signal;

the cell identification means identifies a cell holder where the cell situated at the light irradiation position is retained, and transmits an identification signal of the cell; and, the movement retention unit moves the cell support member along a predetermined track.

19. A particle size distribution analyzer comprising:
multiple cells;
a light source that irradiates light to particles contained in the cells;
multiple photo-detectors that detect the light intensity of a diffraction light or a scattering light generated from the particles irradiated by the light; and
an information processor that calculates a particle size distribution of the particles based upon light intensity signals transmitted from each of the photo-detectors, wherein,
the particle size distribution analyzer further comprises a movement retention unit that retains the multiple cells to be movable between a light irradiation position irradiated by the light and withdrawal positions established at different positions from the light irradiation position;
a stop unit that selectively stops one of the cells at the light irradiation position;
a cell identification means that identifies the cell situated at the light irradiation position and transmits an identification signal of the cell; and
a cell support member that integrally supports the multiple cells;
the information processor is equipped with an operation control program storage where a plurality of operation control programs, each of which is a program for controlling the operation of the particle size distribution analyzer with respect to one of the above-mentioned cells, is stored for each cell; and a program switch means that receives the cell identification signal transmitted from the cell identification means, and automatically switches to another operation control program corresponding to the cell indicated by the cell identification signal;

the cell identification means identifies a cell holder where the cell situated at the light irradiation position is contained, and transmits an identification signal of the cell; and, the movement retention unit is equipped with a rail arranged along a track, and moves the cell support member along the rail, whereby the cell support member can retain multiple different types of cells.

20. The particle size distribution analyzer of claim 19 wherein the multiple cell different types of cells include wet type flow cells and dry type cells.

21. A method of analyzing particle size distribution in a specimen comprising the steps of:
providing a plurality of cells for receiving specimens;
providing a source of light to irradiate one of the plurality of cells at a predetermined position, the plurality of cells are movably mounted to be selectively moved to the predetermined position;
detecting the diffraction or scattering of light from one of the cells at the predetermined position, and providing corresponding detection signals representative of the particle sizes;
calculating a distribution size of the particles in the specimen from the detection signals with one of a plurality of stored operational control programs in an information processor system;
identifying a specific cell from the plurality of cells to be irradiated; and
automatically selecting one of the plurality of stored operation control programs corresponding to the identified cell for calculating the distribution size of the particles in the identified cell.

22. The method of claim 21 wherein the plurality of cells include wet type flow cells and dry type flow cells and further including the step of moving one of the plurality of cells to the predetermined position.

* * * * *